US010568748B2

(12) United States Patent
Asmus et al.

(10) Patent No.: US 10,568,748 B2
(45) Date of Patent: Feb. 25, 2020

(54) CONNECTION DEVICE FOR CONNECTING TWO PROSTHESIS PARTS, AND KIT WITH ONE SUCH CONNECTION DEVICE AND TWO PROSTHESIS PARTS

(71) Applicant: Waldemar Link GmbH & Co. KG, Hamburg (DE)

(72) Inventors: Dörte Asmus, Hamburg (DE); Klaus Dmuschewsky, Hamburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 658 days.

(21) Appl. No.: 15/124,367

(22) PCT Filed: Feb. 26, 2015

(86) PCT No.: PCT/EP2015/054046
§ 371 (c)(1),
(2) Date: Sep. 8, 2016

(87) PCT Pub. No.: WO2015/135762
PCT Pub. Date: Sep. 17, 2015

(65) Prior Publication Data
US 2017/0020689 A1 Jan. 26, 2017

(30) Foreign Application Priority Data
Mar. 10, 2014 (DE) .................. 10 2014 204 326

(51) Int. Cl.
*A61F 2/38* (2006.01)
*A61F 2/46* (2006.01)
*A61F 2/30* (2006.01)
(52) U.S. Cl.
CPC ............ *A61F 2/4684* (2013.01); *A61F 2/384* (2013.01); *A61F 2/3836* (2013.01); *A61F 2002/30476* (2013.01)

(58) Field of Classification Search
CPC ........ A61F 2/384; A61F 2/3845; A61F 2/385; A61F 2/3854; A61F 2/3836; A61F 2/389
See application file for complete search history.

(56) References Cited

U.S. PATENT DOCUMENTS 5,828,867 A 10/1998 Pennell
6,699,293 B2 * 3/2004 White ................. A61F 2/30734
623/22.42
(Continued)

FOREIGN PATENT DOCUMENTS

CN 101969865 A 2/2011
DE 102009007724 A1 8/2010
(Continued)

*Primary Examiner* — Anu Ramana
(74) *Attorney, Agent, or Firm* — Edwin A. Sisson, Attorney at Law, LLC; Jeffrey J. Banyas

(57) ABSTRACT

The invention relates to a connection device for connecting a first and a second prosthesis part, in particular of a tibial and a femoral trial prosthesis for trial arrangement on the corresponding bones, wherein the connection device has a first connection element and a second connection element. The first connection element has inner walls, serving as a guide, and a mating piece and serves for arrangement on the first prosthesis part, and the second connection element is enclosed at least in part by the inner walls of the connection element and is movable in a displacement direction along the inner walls relative to the first connection element and has a groove for receiving a portion of the second prosthesis part. The second connection element is movable, in the direction of displacement relative to the first connection element, to an open position in which the second connection element is at least in part pushed out of the first connection element and the groove of the second connection element is at least in part exposed such that the portion of the second prosthesis part can be inserted into and guided out of the groove, and to a closed position in which the second
(Continued)

connection element is at least in part pushed into the first connection element and the mating piece of the first connection element lies opposite the groove of the second connection element, in such a way that the portion of the second prosthesis part received in the groove is prevented, by the mating piece of the first connection element, from withdrawal from the groove.

20 Claims, 2 Drawing Sheets

(56) References Cited

U.S. PATENT DOCUMENTS

| | | | |
|---|---|---|---|
| 7,025,788 B2* | 4/2006 | Metzger | A61F 2/30721 623/20.15 |
| 8,110,005 B2* | 2/2012 | Berelsman | A61F 2/3804 623/20.11 |
| 8,163,028 B2* | 4/2012 | Metzger | A61F 2/30721 623/20.15 |
| 2012/0330430 A1 | 9/2012 | Meyers et al. | |

FOREIGN PATENT DOCUMENTS

| | | |
|---|---|---|
| DE | 10 2012 001464 A1 | 8/2013 |
| EP | 0923916 A1 | 6/1999 |
| FR | 2848412 A1 | 6/2004 |

* cited by examiner

CONNECTION DEVICE FOR CONNECTING TWO PROSTHESIS PARTS, AND KIT WITH ONE SUCH CONNECTION DEVICE AND TWO PROSTHESIS PARTS

PRIORITIES AND CROSS REFERENCES

This patent application claims the priority from International Application No. PCT/EP2015/054046 filed on 26 Feb. 2015 and German Patent Application No. 102014204326.3filed on 10 Mar. 2014 the teachings of both of which are incorporated herein by reference in their entirety.

TECHNICAL FIELD

The invention relates to a connection device for connecting a first and a second prosthesis part, in particular a tibial and a femoral trial prosthesis for trial arrangement on the corresponding bones. The first connection element serves for mounting on the first prosthesis part, and the second connection element serves to receive a portion of the second prosthesis part. The second connection element is displaceable relative to the first connection element.

PRIOR ART

Connection devices of the type mentioned above are widely used in joint prostheses. In particular in knee joint prostheses, the connection device allows the femoral condyles to be connected to a tibial support surface.

The suitability of prostheses in terms of rotation, flexion and hyperextension should already be established during surgery. For this, trial prostheses may be used which are temporarily inserted during surgery prior to insertion of the final prostheses.

These trial prostheses are conventionally connected by screwing together two jaws which clamp a ridge between femoral condyles. However, screw connections have the disadvantage that fastening is complicated and difficult to do with only one hand during surgery.

Another connection possibility is disclosed in EP 0 923 916 A1, where a peg is provided with a circumferential protrusion in which the ridge between femoral condyles can be received. The peg can be slid into the tibial prosthesis.

Connection devices of this type have proven their worth. However, increased demands are being placed on such connection devices in terms of reliability as to unintentional detachment, stable guidance by the connection components as well as handling.

SUMMARY OF THE INVENTION

It is thus an object of the present invention to improve the handling and reliability of a connection device for connecting two prosthesis parts which is of simple construction. In particular, a connection device is to be provided which allows for a connection between two prosthesis parts to be easily established and handled during surgery. Furthermore, the connection device is supposed to allow for defined mounting and precise guidance of the two trial prostheses relative to one another.

This object is attained according to the invention by the connection device having the feature of claim 1. In accordance therewith, the connection device comprises a first connection element having inner walls serving as a guide and a mating piece, for mounting on the first prosthesis part, and a second connection element which is, at least in part, enclosed by the inner walls of the first connection element and is displaceable along the inner walls relative to the first connection element in a displacement direction and has a groove for receiving a portion of the second prosthesis part. The second connection element is displaceable, in the displacement direction relative to the first connection element, to an open position in which the second connection element is, at least in part, slid out of the first connection element, and the groove of the second connection element is, at least in part, exposed such that the portion of the second prosthesis part can be introduced into and withdrawn from the groove, and to a closed position in which the second connection element is, at least in part, slid into the first connection element, and the mating piece of the first connection element is disposed opposite the groove of the second connection element in such a blocking way that the portion of the second prosthesis part received in the groove is prevented by the mating piece of the first connection element from exiting the groove.

The connection device according to the invention allows the second connection element to be stably guided by the guide in the first connection element based on the inner walls of the first connection element. In addition, the connection device according to the invention restricts the trial prosthesis in terms of rotation, flexion and hyperextension. The ROM ("range of motion") corresponds to that of the implants to be permanently inserted later on and enables rotation of ±15 degrees, flexion of 120 degrees, and hyperextension of 2.5 degrees. The defined displaceability to two positions makes it possible at the same time to displace the second connection element to a position in which the portion of the second prosthesis part can be inserted into or withdrawn from the groove, and to a closed position differing therefrom, in which the groove is disposed opposite the mating piece in such a way that the groove is substantially closed and the portion of the second prosthesis part is unable to exit the groove. It can thus be ensured that there is a reliable connection between the first and the second prosthesis part as long as the connection device or the second connection element is in the closed position. Only in the open position can the first and the second prosthesis part be separated. To switch between the two positions, the second connection element just needs to be displaced relative to the first connection element.

Different sizes of the connection device according to the invention can be used in accordance with the sizes of the trial prostheses or implants. A special connection device of smaller dimensions should in particular be used for small sizes.

The invention is based on the idea of providing a connection device for reliable and easy-to-handle connection between a first and a second prosthesis part, wherein it is possible, due to stable and defined guidance, to displace the second connection element so that the second prosthesis part can be received or removed in one position and the portion of the second prosthesis part is safely received in another position. The change in position is accomplished by displacing the first and the second connection element relative to one another so that a "screwless" connection is enabled between two prosthesis parts. Thus, neither a screw nor a thread is involved in establishing or releasing the connection.

The mating piece which is disposed opposite the groove so as to close the groove may, in particular, also form part of the inner walls serving as a guide.

The second connection element is, in other words, slidably mounted in the first connection element and is circumferentially enclosed by the first connection element or the inner walls of the first connection element.

Moreover, the displacement direction must be understood to mean the directions in which the relative motion between the first and the second connection element takes place during the transition from the open to the closed and from the closed to the open position. The direction of displacement toward the open position is opposed to the direction of displacement toward the closed position.

Particularly advantageous developments of the invention are set forth in the dependent claims.

The mating piece is preferably configured as a protrusion which, in the connecting direction, protrudes from the first connection element toward the open position. In other words, the mating piece may upwardly protrude. This advantageously allows the groove to be closed or covered, whilst at the same time reducing the distance to be covered in the displacement direction between the open position and the closed position.

In particular, the groove extends substantially perpendicular to the displacement direction. It is moreover preferred that the groove defines an opening which is open substantially perpendicular to the displacement direction. In other words, the opening of the groove is oriented perpendicular to the displacement direction. Thus, during displacement of the second connection element in the displacement direction, one of opposite walls of the groove may carry along, in the displacement direction, the portion of the second prosthesis part received in the groove. This orientation of the groove or opening thus makes it possible to both easily insert and withdraw a received portion and to displace the second connection element, without the received portion slipping out unintentionally, for example. The mating piece may be configured as a protrusion in such a way as to protrude upwardly from the first connection element as a substantially vertical plate portion so that the vertically open groove can be well covered by the vertical mating piece.

The first connection element may comprise a spring member, particularly a spring clip, for pressing against the second connection element, thereby preventing unintentional displacement of the second connection element in the displacement direction. As a consequence, the spring clip exerts a friction force in pressing against the second connection element, in particular when this is supposed to be displaced toward the open position. This force can be easily overcome where displacement is intended; in the event of an unintentional displacement, however, displacement of the second connection element relative to the first connection element can be prevented.

It is preferred that the spring member is arranged with respect to the mating piece in the displacement direction toward the closed position, the spring member thus being positioned below the mating piece. It is particularly appropriate that a spring clip extends from the mating piece to the bottommost portion of the first connection element.

The second connection element preferably comprises a stepped portion and the first connection element comprises a complementary stop such that maximum displacement of the second connection element relative to the first connection element in the open position is restricted by abutment of the stepped portion and the stop against one another. Complete, unintentional detachment of the second connection element from the first connection element can thus be prevented.

According to the invention, there is provided a kit with a connection device according to the invention, a first prosthesis part and a second prosthesis part. The portion of the second prosthesis part to be received in the second connection element is preferably configured as an axis transverse to the displacement direction and with a cross-section corresponding substantially to the cross-section of the free surface of the groove of the second connection element. This allows the portion of the second prosthesis part to be received in the second connection element substantially without clearance, thereby precisely defining, in particular, the guidance or mounting and orientation of the first prosthesis part relative to the second prosthesis part.

The first prosthesis part preferably comprises a guide for the first connection element in a direction perpendicular to the displacement direction, for mounting of the first connection element on the first prosthesis part. This also makes it possible to easily fasten the first connection element to the tibial trial prosthesis, with the position of the first connection element being secured in the displacement direction, i.e. perpendicular to the guide in the first prosthesis part, so that during displacement of the second connection element relative to the first connection element in the displacement direction the first connection element is held in a defined manner in the first connecting direction.

Both the first and the second prosthesis part are preferably composed of a metal, metal alloy, plastic and/or ceramic.

Further features and advantages of the invention will become more apparent from the following detailed description.

DETAILED DESCRIPTION OF A PREFERRED EMBODIMENT

One preferred embodiment of the present invention will now be described in detail with reference to the accompanying drawings.

Here the first connection element 1 is configured substantially as a sleeve and the second connection element 2 as a base part receiving the axle bolt of a femoral trial prosthesis in a groove or retaining groove. The second connection element 2 is configured substantially as an elongate body with round cross-section.

Figure 1:
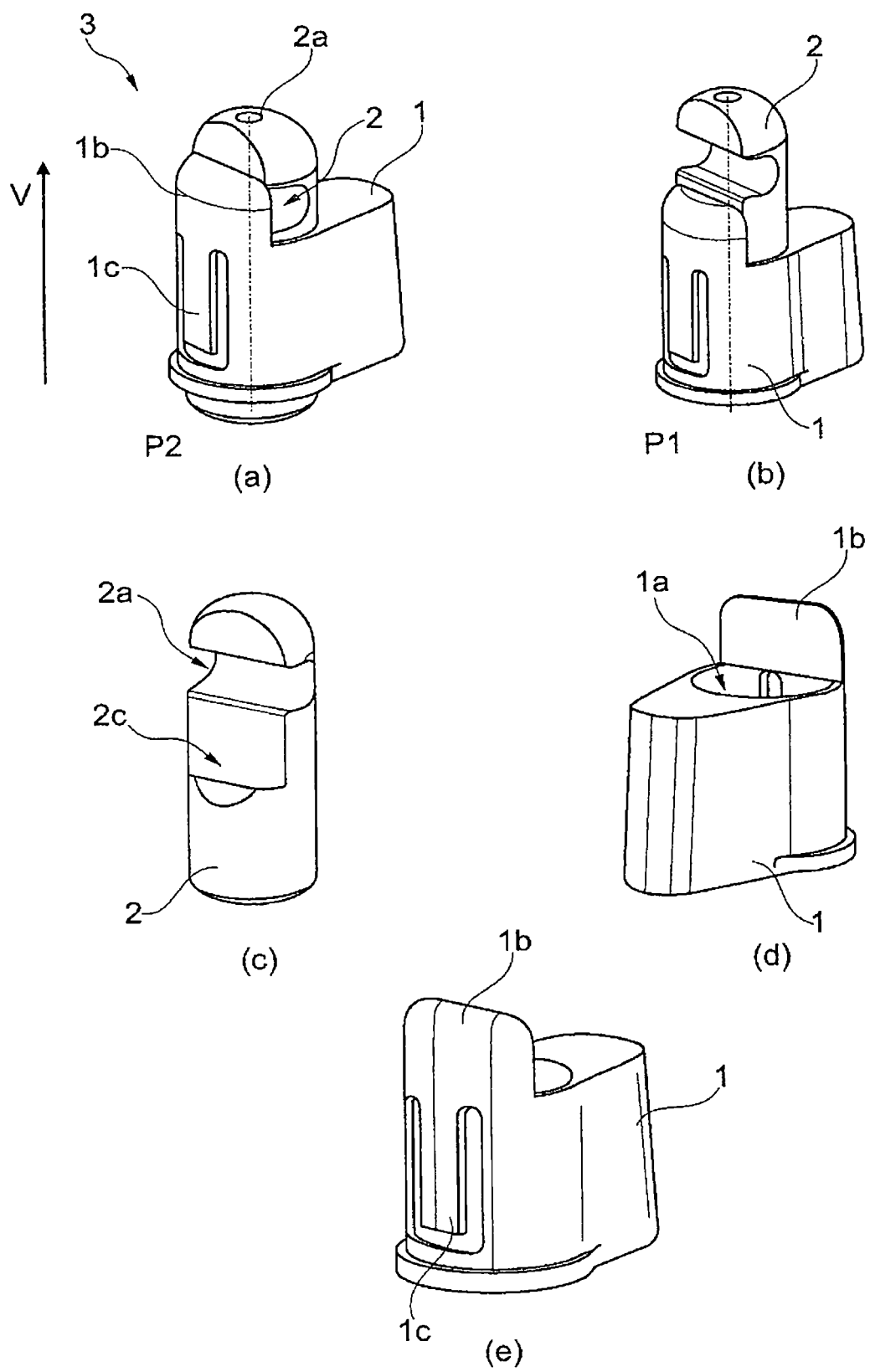
FIG. 1(a) shows a first connection element and a second connection element according to the present invention in the closed position.
FIG. 1(b) shows a first connection element and a second connection element according to the present invention in the open position.
FIG. 1(c) shows a second connection element according to the present invention.
FIG. 1(d) is a front view of a first connection element according to the present invention.
FIG. 1(e) is a rear view of a first connection element according to the present invention.

FIG. 1(a) shows a connection device 3 with a first connection element 1 and a second connection element 2. The first connection element 1 comprises a mating piece 1b and a spring clip 1c. The second connection element 2 comprises a groove 2a. The connection device shown in FIG. 1(a) is in the closed position P2, and the second connection element is displaced to the closed position P2 relative to the first connection element. In this closed position P2, the second connection element 2 is, at least in part, slid into the first connection element 1, and the mating piece 1b of the first connection element 1 is disposed opposite the groove 2a of the second connection element 2 in such a blocking way that the portion IIa received in the groove 2a is prevented by the mating piece 1b of the first connection element from exiting the groove 2a.

FIG. 1(b) shows the open position P1 in which the second connection element 2 is, at least in part, slid out of the first connection element 1, and the groove 2a of the second connection element is, at least in part, exposed or uncovered such that a portion IIa which is, or is to be, received can be inserted into or withdrawn from the groove.

The second connection element 2 is displaceably received in the first connection element 1 so as to be displaceable in the displacement direction V relative to the first connection element 1. Thus, the transition from the closed position shown in FIG. 1(a) to the open position shown in FIG. 1(b) is effected by displacing the first and the second connection element in the displacement direction V which is vertical in the Figures.

FIG. 1(c) shows the second connection element 2 having the groove 2a extending perpendicular to the displacement direction V. The groove 2a defines an opening which is such as to be open substantially perpendicular to the displacement direction V. In addition, the second connection element comprises a stepped portion 2c which, in cooperation with a complementary stop (not shown) of the first connection element 1, restricts the maximum displacement of the second connection element 2 relative to the first connection element 1 in the open position P1 in that the stepped portion 2c and the stop abut against each other.

FIG. 1(d) shows a first connection element with the mating piece 1b and the inner walls 1a which serve as a guide for the second connection element 2. The inner walls 1a enclose, at least in part, the second connection element 2 which is displaceable relative to the first connection element 1 along the inner walls 1a in the displacement direction V.

FIG. 1(e) shows another view of the first connection element 1 and, in particular, of the spring member 1c which is capable of pressing against the second connection element 2 in such a way as to prevent unintentional displacement of the second connection element 2 in the displacement direction V toward the open position P1.

It moreover becomes clear from FIG. 1(e) that the spring member 1c, configured as a spring clip, is disposed in the displacement direction V toward the closed position P2. The mating piece 1b may be configured as a protrusion which, in the displacement direction V, protrudes from the first connection element 1 toward the open position.

Figure 2:
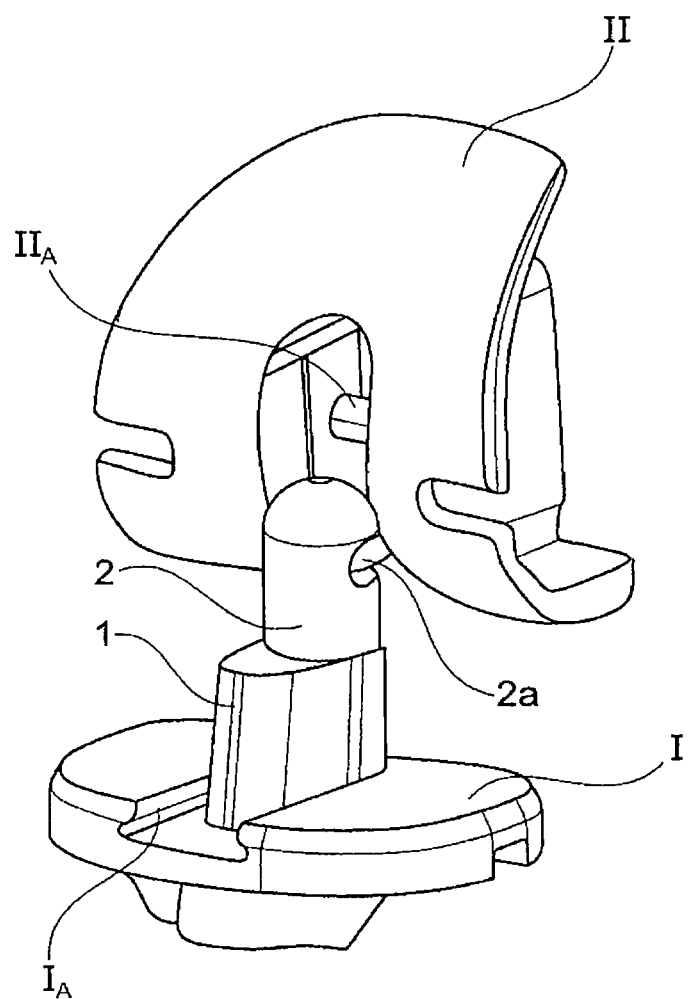
FIG. 2 shows a kit with the connection device, a tibial trial prosthesis and a femoral trial prosthesis according to the present invention.

In addition to the connection device 3 according to the invention with the first connection element 1 and the second connection element 2, FIG. 2 shows a first prosthesis part I which is a tibial trial prosthesis, and a second prosthesis part II which is a femoral trial prosthesis. The first prosthesis part I comprises a guide 1a for passing the first connection element 1 therethrough in a direction perpendicular to the displacement direction V. The guide 1a is configured as a recess which allows the first connection element 1 to be detachably received in the first prosthesis part I.

The second prosthesis part II comprises a portion IIa configured as an axis perpendicular to the displacement direction V. This axis is disposed between two condyle portions of the femoral trial prosthesis. The axial portion IIa has a cross-section corresponding substantially to the cross-section of the free surface of the groove 2a.

The invention claimed is:

1. A connection device for connecting a first and a second prosthesis part said first and second prosthesis part being a tibial and a femoral trial prosthesis for trial arrangement on the corresponding bones, said connection device comprising:
   a first connection element, which comprises inner walls serving as a guide and a mating piece, for mounting on the first prosthesis part, said first prosthesis part being the tibial trial prosthesis, and a second connection element which is, at least in part, enclosed by the inner walls of the first connection element and is displaceable along the inner walls relative to the first connection element in a displacement direction coplanar with a longitudinal axis of the inner walls and has a groove for receiving a portion of the second prosthesis part, said second prosthesis part being of the femoral trial prosthesis,
said second connection element being displaceable, in the displacement direction relative to the first connection element,
   to an open position in which the second connection element is, at least in part, slid out of the first connection element, and the groove of the second connection element is, at least in part, exposed such that the portion of the second prosthesis part can be introduced into and withdrawn from the groove, and
   to a closed position in which the second connection element is, at least in part, slid into the first connection element, and the mating piece of the first connection element is disposed opposite the groove of the second connection element in such a blocking way that the portion of the second prosthesis part received in the groove is prevented by the mating piece of the first connection element from exiting the groove.

2. A connection device according to claim 1, wherein the mating piece is configured as a protrusion which, in the displacement direction toward the open position, protrudes from the first connection element.

3. A connection device according to claim 2, wherein the groove defines an opening which is open substantially perpendicular to the displacement direction.

4. A connection device according to claim 2, wherein the first connection element comprises a spring member, said spring member being a spring clip, for pressing against the second connection element in such a way that unintentional displacement of the second connection element in the displacement direction toward the open position is prevented.

5. A connection device according to claim 4, wherein the spring member is arranged with respect to the mating piece in the displacement direction toward the closed position.

6. The connection device according to claim 2, wherein the second connection element comprises a stepped portion, and the first connection element comprises a complementary stop such that maximum displacement of the second connection element relative to the first connection element in the open position is restricted by abutment of the stepped portion and the stop against one another.

7. A kit with a connection device according to claim 2, a first prosthesis part and a second prosthesis part, the first prosthesis part being a tibial trial prosthesis and the second prosthesis part being a femoral trial prosthesis, for trial arrangement on the corresponding bones, wherein a portion of the second prosthesis part is configured perpendicular to the displacement direction.

8. A kit according to claim 7, wherein the first prosthesis part comprises a guide for the first connection element, for mounting of the first connection element on the first prosthesis part in a direction perpendicular to the displacement direction.

9. A connection device according to claim 1, wherein the groove defines an opening which is open substantially perpendicular to the displacement direction.

10. A connection device according to claim 9, wherein the first connection element comprises a spring member, said spring member being a spring clip, for pressing against the second connection element in such a way that unintentional displacement of the second connection element in the displacement direction toward the open position is prevented.

11. The connection device according to claim 9, wherein the second connection element comprises a stepped portion, and the first connection element comprises a complementary stop such that maximum displacement of the second connection element relative to the first connection element in the open position is restricted by abutment of the stepped portion and the stop against one another.

12. A kit with a connection device according to claim 9, a first prosthesis part and a second prosthesis part, the first prosthesis part being a tibial trial prosthesis and the second prosthesis part being a femoral trial prosthesis, for trial arrangement on the corresponding bones, wherein a portion of the second prosthesis part is configured perpendicular to the displacement direction.

13. The connection device according to claim 1, wherein the second connection element comprises a stepped portion, and the first connection element comprises a complementary stop such that maximum displacement of the second connection element relative to the first connection element in the open position is restricted by abutment of the stepped portion and the stop against one another.

14. A kit with a connection device according to claim 1, a first prosthesis part and a second prosthesis part, the first prosthesis part being a tibial trial prosthesis and the second prosthesis part being a femoral trial prosthesis, for trial arrangement on the corresponding bones, wherein a portion of the second prosthesis part is configured perpendicular to the displacement direction.

15. A kit according to claim 14, wherein the first prosthesis part comprises a guide for the first connection element, for mounting of the first connection element on the first prosthesis part in a direction perpendicular to the displacement direction.

16. A connection device for connecting a first and a second prosthesis part said first and second prosthesis part being a tibial and a femoral trial prosthesis for trial arrangement on the corresponding bones, said connection device comprising:
    a first connection element, which comprises inner walls serving as a guide and a mating piece, for mounting on the first prosthesis part, said first prosthesis part being the tibial trial prosthesis, and
    a second connection element which is, at least in part, enclosed by the inner walls of the first connection element and is displaceable along the inner walls relative to the first connection element in a displacement direction coplanar with a longitudinal axis of the inner walls and has a groove for receiving a portion of the second prosthesis part, said second prosthesis part being of the femoral trial prosthesis,
said second connection element being displaceable, in the displacement direction relative to the first connection element,
    to an open position in which the second connection element is, at least in part, slid out of the first connection element, and the groove of the second connection element is, at least in part, exposed such that the portion of the second prosthesis part can be introduced into and withdrawn from the groove, and
    to a closed position in which the second connection element is, at least in part, slid into the first connection element, and the mating piece of the first connection element is disposed opposite the groove of the second connection element in such a blocking way that the portion of the second prosthesis part received in the groove is prevented by the mating piece of the first connection element from exiting the groove, and
wherein the first connection element comprises a spring member, said spring member being a spring clip, for pressing against the second connection element in such a way that unintentional displacement of the second connection element in the displacement direction toward the open position is prevented.

17. A connection device according to claim 16, wherein the spring member is arranged with respect to the mating piece in the displacement direction toward the closed position.

18. The connection device according to claim 17, wherein the second connection element comprises a stepped portion, and the first connection element comprises a complementary stop such that maximum displacement of the second connection element relative to the first connection element in the open position is restricted by abutment of the stepped portion and the stop against one another.

19. A kit according to claim 18, wherein the first prosthesis part comprises a guide for the first connection element, for mounting of the first connection element on the first prosthesis part in a direction perpendicular to the displacement direction.

20. The connection device according to claim 16, wherein the second connection element comprises a stepped portion, and the first connection element comprises a complementary stop such that maximum displacement of the second connection element relative to the first connection element in the open position is restricted by abutment of the stepped portion and the stop against one another.

* * * * *